(12) United States Patent
Huntzinger et al.

(10) Patent No.: US 8,890,100 B2
(45) Date of Patent: *Nov. 18, 2014

(54) INTERNALLY MOUNTED COLLIMATORS FOR STEREOTACTIC RADIOSURGERY AND STEREOTACTIC RADIOTHERAPY

(75) Inventors: Calvin J. Huntzinger, San Carlos, CA (US); David K. Jensen, Sunnyvale, CA (US); William A. Strachan, San Francisco, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/585,838

(22) Filed: Aug. 15, 2012

(65) Prior Publication Data

US 2014/0048727 A1    Feb. 20, 2014

(51) Int. Cl.
*A61N 5/10* (2006.01)
*G21K 1/02* (2006.01)

(52) U.S. Cl.
USPC ................ 250/505.1; 378/147; 250/503.1

(58) Field of Classification Search
CPC ..... A61N 5/10; A61N 5/1042; A61N 5/1064; A61N 5/1048; A61N 5/1045; A61N 5/1067; A61N 5/1071; G21K 1/02
USPC ........... 250/306, 307, 492.1, 492.21, 492.22, 250/492.23, 492.3, 498.1, 503.1, 505.1
See application file for complete search history.

(56) References Cited

U.S. PATENT DOCUMENTS

| | | | | |
|---|---|---|---|---|
| 2,730,566 | A | * | 1/1956 | MacLaughlin, Jr. et al. ............... 378/98.6 |
| 3,767,931 | A | * | 10/1973 | Williams ................. 378/153 |
| 4,109,154 | A | * | 8/1978 | Taumann ................. 378/159 |
| 4,172,979 | A | * | 10/1979 | Morrison ................... 378/65 |
| 4,627,089 | A | * | 12/1986 | Menor et al. ............. 378/157 |
| 5,012,506 | A | * | 4/1991 | Span et al. ............... 378/152 |
| 5,917,883 | A | * | 6/1999 | Khutoryansky et al. .... 378/116 |
| 5,945,684 | A | * | 8/1999 | Lam et al. ............... 250/492.3 |
| 6,353,655 | B1 | * | 3/2002 | Siochi ...................... 378/65 |
| 6,389,108 | B1 | * | 5/2002 | Ein-Gal .................. 378/147 |
| 7,132,674 | B2 | * | 11/2006 | Pastyr et al. ........... 250/505.1 |
| 7,763,873 | B2 | * | 7/2010 | Flynn et al. ............ 250/505.1 |
| 7,852,990 | B2 | * | 12/2010 | Aulbach ................. 378/148 |
| 8,077,830 | B2 | * | 12/2011 | Brown et al. ........... 378/156 |
| 2002/0131556 | A1 | * | 9/2002 | Steinberg ............... 378/152 |
| 2003/0091146 | A1 | * | 5/2003 | Siochi ...................... 378/65 |
| 2010/0012829 | A1 | * | 1/2010 | Islam et al. ............ 250/252.1 |
| 2010/0034357 | A1 | * | 2/2010 | Svesson et al. ........... 378/152 |
| 2010/0254514 | A1 | * | 10/2010 | Evans et al. ............... 378/86 |

(Continued)

OTHER PUBLICATIONS

Cosgrove VP, Jahn U, Pfaender M, Bauer S, Budach V, Wurm R. Commissioning of a micro multi-leaf collimator and planning system for stereotactic radiosurgery. Radiother Oncol. 1999; 50: 325-336.*

*Primary Examiner* — Brooke Purinton
(74) *Attorney, Agent, or Firm* — Houst Consulting

(57) ABSTRACT

A beam filter positioning device includes a first and a second axes operable to move a body supporting one or more collimators, one or more photon flattening filters, one or more electron foils, and field light mirror etc. The collimators may be configured to collimate radiation to define a treatment beam suitable for radiosurgery. A controller is programmed to control the servo motor of the first and second axes to accurately position the beam filters. Radiation apparatuses and systems incorporating the beam filter positioning device or assembly are also provided.

28 Claims, 12 Drawing Sheets

(56) References Cited

U.S. PATENT DOCUMENTS

| | | | |
|---|---|---|---|
| 2011/0057110 A1* | 3/2011 | Testa et al. | 250/370.07 |
| 2011/0293067 A1* | 12/2011 | Stahl et al. | 378/65 |
| 2012/0043481 A1* | 2/2012 | Mansfield et al. | 250/492.1 |
| 2013/0261430 A1* | 10/2013 | Uhlemann | 600/411 |

* cited by examiner

INTERNALLY MOUNTED COLLIMATORS FOR STEREOTACTIC RADIOSURGERY AND STEREOTACTIC RADIOTHERAPY

RELATED APPLICATIONS

This application is related to U.S. application Ser. No. 12/568,619, filed Sep. 28, 2009 and entitled "Beam Filter Positioning Device," the disclosure of which is incorporated herein by reference in its entirety.

BACKGROUND

This disclosure relates generally to radiation apparatuses and methods and in particular to beam filter positioning devices and radiation apparatuses and systems incorporating the beam filter positioning devices, which are useful in radiation therapy including radiosurgery such as stereotactic radiosurgery (SRS) and stereotactic body radiotherapy (SBRT).

Radiosurgery is a highly precise, intensified form of radiation therapy. Stereotactic radiosurgery (SRS) has been used to treat brain disorders such as brain tumors and lesions. Conventionally, SRS cones are used with linear accelerators to help achieve precise delivery of high dose radiation. SRS cones are typically made from tungsten and have a conical hole through which radiation passes creating a focused treatment beam. In the prior art, SRS cones are installed on a mount assembly, which is externally attached to an interface mount on a linear accelerator.

The conventional scheme for using externally mounted SRS cones is time consuming and labor intensive. Further, externally mounted SRS cones may present a potential collision hazard with the treatment couch or the patent.

SUMMARY

Beam filter positioning devices or assemblies including one or more collimators such as SRS collimators are provided. Radiation apparatuses and systems incorporating the beam filter positioning devices or assemblies are also provided. Other embodiments are described further herein.

DETAILED DESCRIPTION

Figure 1:
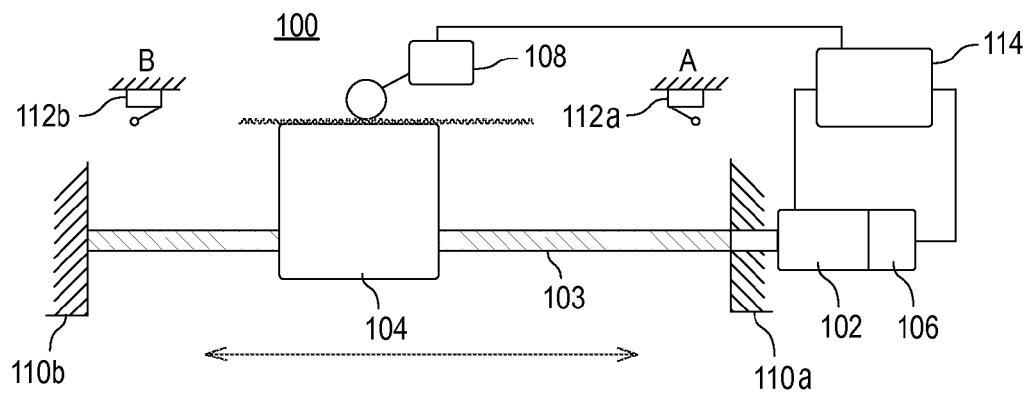
FIG. 1 is a schematic representation of a linear axis in accordance with some embodiments of the disclosure.

Various embodiments of beam filter positioning devices and apparatuses and systems incorporating the devices are described. While various embodiments are described in connection with stereotactic radiosurgery (SRS), it will be appreciated that the assemblies, apparatuses and systems can also be used to perform other forms of radiation therapy. The terminology used herein is for the purpose of describing particular embodiments and is not intended to be limiting since the scope of the invention will be defined by the appended claims, along with the full scope of equivalents to which such claims are entitled.

Various relative terms such as "above," "under," "upper," "over," "on," "top," "bottom," "higher," and "lower" etc. may be used to facilitate description of various embodiments. The relative terms are defined with respect to a conventional orientation of a structure, which may not necessarily represent an actual orientation of the structure in manufacture or use. The following detailed description is, therefore, not to be taken in a limiting sense. As used in the description and appended claims, the singular forms of "a," "an," and "the" include plural references unless the context clearly dictates otherwise. Thus, for example, reference to "an SRS collimator" may include one or more SRS collimators, and reference to "the beam filter" may include one or more beam filters described herein.

As used herein, the term "axis" refers to a mechanism that is operable to move an object in a direction. For example, a "linear axis" refers to a mechanism that is operable to move an object in a linear direction. A "rotational axis" refers to a mechanism that is operable to rotate an object in an angular direction. An axis may preferably include a servo motor and one or more feedback devices that are electrically coupled to a control mechanism operable with user interface software. A close loop control can be used to control the axis and automatically adjust the position of an object in a system.

As used herein the term "beam filter" refers to a member that modulates one or more parameters of a particle beam such as the energy, intensity, shape, direction, dose distribution, or other beam parameters. A particle beam includes but is not limited to a beam of electrons, photons, protons, heavy ions, or other particles. By way of example, a beam filter includes but is not limited to a photon flattening filter, an electron scattering foil, a proton scattering foil, and a collimator such as an SRS collimator.

As used herein the term "radiosurgery" refers to an intensified form of radiation therapy in which focused high energy radiation is precisely delivered to a target. Radiosurgery is therefore generally performed in fewer sessions than conventional radiation therapy. Stereotactic radiosurgery (SRS) refers to the treatment of tumors or lesions or abnormalities in the brain or spinal column. Stereotactic body radiation therapy (SBRT) is typically used for targets that are outside the brain and the spine. SBRT is most commonly used for targets in the lung, liver, pancreas, breast, prostate, and kidney. The targets of radiosurgery are generally small compared to radiotherapy targets, such as targets with a largest dimension less than about 30 mm.

This disclosure provides an assembly which includes a body, one or more collimators supported by the body, and one or more axes operable to move the body. Each of the collimators may have a hole configured to define the shape of a treatment beam useful e.g. in radiotherapy, radiosurgery, or stereotactic radiosurgery. The hole may be in conical, cylindrical or other suitable shape. Advantageously, the collimators can be optimized and supported by a body that optionally carries other beam filters such as photon flattening filters, electron scattering foils, etc. Therefore, the collimators can be advantageously placed in the treatment head of a radiation apparatus. Motion axes and control systems that are used to move and control positions of the other beam filters can be used to move and control the positions of collimators.

One or more, and in some embodiments, two or more motion axes can be used to move the body supporting the collimators. The motion axes can be linear axes or rotational axes, or any combination of linear and rotational axes. For example, the motion axes may include a linear axis operable to translate the body and a rotational axis operable to rotate the body. In some embodiments, the assembly can be designed such that the linear axis is operable to support and translate the rotational axis which operates to rotate the body and the collimators. In other words, the rotational axis that operates to rotate the body and the collimators can be further moved by the linear axis in a linear direction. While it is not intended to limit the scope of the appended claims, in some embodiments, the assembly including a body supporting or carrying the collimators and optionally other beam filters, may be analogous to a rotatable carousel, which is further movable in a linear direction. Alternatively, the assembly can be designed such that the rotational axis is operable to support and rotate the linear axis which operates to translate the body and the collimators. That is, the linear axis which operates to translate the body and the collimators in a linear direction can be supported and rotated by the rotational axis. In alternative embodiments, two or more linear axes can be used to move the body supporting the collimators.

In some embodiments, the body supporting the collimators may support and/or carry additional beam filters such as one or more photon flattening filters, one or more electron scattering foils, and elements for field light simulation such as a mirror. The collimators, photon flattening filters, electron scattering foils, and other elements can be arranged in any suitable configurations on the supporting body. By way of example, one or more collimators and one or more photon flattening filters can be arranged in a circular or an arc configuration having a first radius. One or more electron scattering foils can be arranged in a circular or an arc configuration having a second radius different from the first radius. The electron scattering foils can be arranged outer of the collimators and/or photon flattening filters. Alternatively, the collimators and/or photon flattening filters can be arranged outer of the electron scattering foils. In alternative embodiments, the collimators, photon flattening filters, electron scattering foils, and other elements can be arranged in other suitable configurations such as a running track configuration with two semi-circles connected with straight lines.

The assembly may further include a target assembly and an axis operable to move a target to a desired location. An ion chamber assembly may also be included in the assembly and an axis can be used to move an ion chamber to a desired location. Therefore, in a preferred embodiment, the assembly may include two axes for moving a body supporting collimators and/or other beam filters, one axis for moving a target assembly, and one axis for moving an ion chamber assembly. Such an assembly can be supported by a support body as a modular structure, which can be disposed as a unit and secured in a treatment head. Each of the four axes may include a servo motor coupled to a control system operable with user interface software. The control system may control the motion axes to simultaneously or sequentially move the collimators, photon flattening filters, electron scattering foils, field light simulation elements, targets, and ion chambers to their desired locations in a coordinated manner.

In some embodiments the disclosure provides a radiation apparatus such as a linear accelerator which includes a treatment head and one or more SRS collimators placed in the treatment head. In particular, the radiation apparatus includes a radiation source having a target configured to produce radiation when impinged by electrons, and one or more SRS collimators residing in the treatment head. The one or more SRS collimators are configured to collimate the radiation to provide a treatment beam suitable for stereotactic radiosurgery.

The target may reside in the treatment head. Alternatively, the target may reside outside the treatment head. The SRS collimators may have a through hole configured to define the shape of a treatment beam at the isocenter. The through hole in the SRS collimators may be in conical, cylindrical or other suitable shape. The SRS collimators may be moved relative to the radiation source so that an SRS collimator with a particularly sized hole can be selected for a planned SRS operation. In some embodiments, the SRS cones may be positioned adjacent to the patient.

The SRS collimators can be supported or carried by any suitable body member and moved by any suitable motion axis or axes. In general, any positioning device and motion axes can be used to position the SRS collimators with sufficient accuracy. In some preferred embodiments, the SRS collimators can be placed in a beam filter positioning device or assembly as described above, which supports or carries photon flattening filters, electron scattering foils, and field light mirror, etc.

Therefore, in some embodiments, a body member may support SRS collimators, photon flattening filters, electron foils, and a field light mirror. The SRS collimators and photon flattening filters may be arranged in a circular or an arc configuration having a first radius, and the electron scattering foils may be arranged in a circular or an arc configuration having a second radius. The electron scattering foils can be arranged at a different radius from that of the SRS collimators and/or photon flattening filters. The body member supporting SRS collimators and various other beam filters can be moved by one or more, or two or more motion axes. The motion axes can be linear axes or rotational axes, or any combination of linear and rotational axes. For example, the body member can be moved by a combination of a linear axis and a rotational axis, in which the rotational axis may be supported and further translated by the linear axis. Alternatively, the body member can be moved by a combination of a linear axis and a rotational axis, in which the linear axis can be supported and further rotated by the rotational axis. A combination of two or more linear axes can also be used to move the body member.

The disclosure further provides a radiation system. The radiation system may include a control system which is operable with user interface software and programmed to control motion axes which are designed to move various devices or components such as SRS collimators, photon flattening filters, electron scattering foils, a field light mirror, targets, and an ion chamber etc. The motion axes may include servo motors and feedback devices which are coupled to the control system. The control system may be programmed to command the servo motors such that the motion axes may move devices or components to desired locations. The control system may also receive signals from the feedback devices and command the servo motors based on the feedback signals so that the positions of SRS collimators or other beam filters, targets, or ion chamber etc. can be automatically adjusted.

Exemplary embodiments are now described with reference to the figures. It should be noted that the figures are not drawn to scale, and are only intended to facilitate the description of specific embodiments. They are not intended as an exhaustive description or as a limitation on the scope of the invention.

Figure 2:
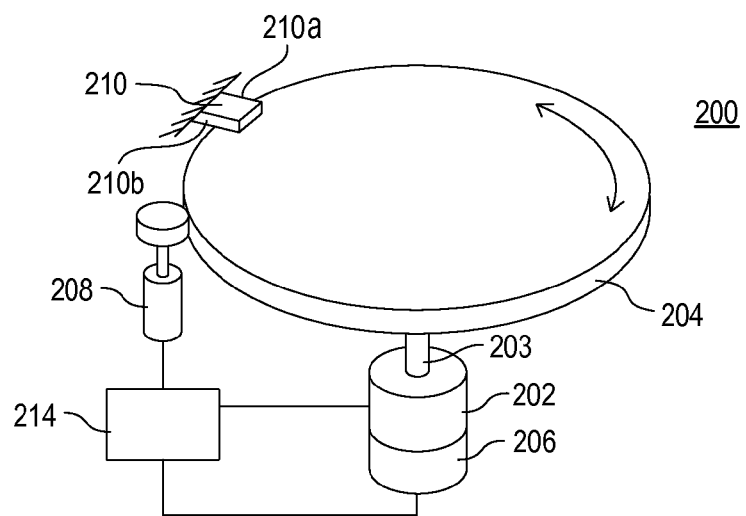
FIG. 2 is a schematic representation of a rotational axis in accordance with some embodiments of the disclosure.

FIGS. 1 and 2 illustrate an exemplary linear axis 100 and rotational axis 200 respectively, which can be used in the assemblies or apparatuses of the disclosure. The linear axis 100 and rotational axis 200 may respectively include a motor 102, 202, a load 104, 204 coupled to the motor 102, 202, and one or more feedback devices 106, 108, 206, 208. The load 104, 204 may include a body supporting one or more collimators such as SRS collimators according to some embodiments. The load 104, 204 may also be an energy switch assembly, a target assembly, a beam filter assembly, an ion chamber assembly, a collimation assembly, an MLC assembly, or a treatment couch. The load 104, 204 may further be various other devices, units, components, or a body supporting one or more of the above described devices, units, components or assemblies. The feedback device 106, 206 may be coupled to the motor shaft to provide feedback signals which may be used to measure the position and/or velocity of the motor. The feedback device 108, 208 may be coupled to the load 104, 204 to provide feedback which may be used to measure the position and/or velocity of the load. One or more feedback devices may be coupled to the motor 102, 202 and/or one or more feedback devices coupled to the load 104, 204 respectively to provide feedback on the position and/or velocity of the motor and the load respectively. One or more feedback devices may also be coupled to the load 104, 204 each of which may independently provide feedback on the position and/or velocity of the load. The motor 102, 202 and feedback devices 106, 108, 206, 208 may be electrically coupled to a controller 114, 214. Structural features 110a, 110b, 210a, 210b define the end-of-travel of the axis 100, 200 and the range of travel of the axis. The structural features 110a, 110b, 210a, 210b can be fixed structures or hardstops the locations of which will not be changed for the life of the system. As used herein, the structural features 110a, 110b can be two independent or separate hardstops (e.g. in FIG. 1), or the structure features 210a, 210b can be one hardstop with two hard contact surfaces (e.g. in FIG. 2).

The linear axis 100 and rotational axis 200 may optionally include limit switches or sensors 112a, 112b (shown in FIG. 1 not in FIG. 2) located near the hardstops. When triggered, the limit switches or sensors may signal the controller 114, 214 that the axis is approaching an end of travel. The controller 114, 214 may then reduce the axis speed and lower the peak torque capacity of the motor to avoid collision damage to the axis and increase positioning accuracy.

The motors 102, 202 are preferably a servo motor such as brush servo motors, brush-less servo motors, stepper motors, linear motors, servo-controlled dual-cylinder pneumatic/hydraulic drives, or any other suitable motors. Various motors are known in the art and their detail construction is omitted herein for clarity of the description of the disclosure. The motors 102, 202 may be coupled to the load via various suitable means. For example in FIG. 1, a ball screw 103 may engage with the load 104 and be coupled to the motor 102 via a coupler. In operation the motor 102 may rotate the ball screw 103, which in turn translates the load 104 in a linear direction. In FIG. 2, a shaft 203 may engage the load 204 e.g. via a bearing assembly and be coupled to the motor 202 via a coupler. The motor 202 rotates the shaft 203, which in turn rotates the load 204 in an angular direction. Any other means of coupling known in the art may be used to transmit the driving force from the motor to the load. For example, timing belt, pulleys, rollers, nuts, guides and various other units may be used to drivingly couple the load to the motor.

The feedback devices 106, 108, 206, 208 may be relative, incremental, or absolute feedback devices. The feedback devices and the controller keep track of the overall absolute positions throughout the range of motion of the axis. For example, the feedback devices can be optical encoders, magnetic encoders, transducer encoders such as resolvers or linear varying differential transducers (LVDT), and capacitive encoders. The feedback devices can be linear or rotary encoders, absolute or incremental encoders. Various encoders, resolvers, Hall sensors, tachometers and potentiometers are known in the art and commercially available and thus their detail construction is not described herein. In general, a rotary encoder is a position feedback device that sends a digital pulse as exact angular increments about a single revolution. An incremental encoder can also send an index pulse at every revolution at the same rotational angle of the device. A resolver is a rotary position feedback device that gives absolute position through one full revolution. The voltage value generated when a resolver is rotated to exactly 0 degree is called null voltage. A series of Hall sensors may be used e.g. in a brushless electric motor to detect the position of the permanent magnet. Hall sensors are typically used for motor commutation, but a system of Hall sensors, for the purpose of homing, can be considered a positioning device since it gives distinct position information of the motor per revolution. A tachometer is an analog device which returns an electrical signal (voltage) as proportional to rotation speed. A tachometer is a feedback for shaft rotational velocity. A potentiometer is an analog device which returns an electrical signal (resistance) as a function of rotation angle. A potentiometer is an angular positioning sensor. By way of example, when a feedback device such as an encoder or a resolver is coupled to a motor, the position of the rotating motor shaft can be ascertained and the position of the load connected to the motor shaft calculated by counting pulses or reading the voltages in the direction of rotation and tracking the revolutions of the encoder or resolver. For example, when a home or reference position has been established for an axis, the controller may capture the angle of the feedback device and resets the device at the reference position. As the axis is commanded to move from the reference position, the controller receives subsequent pulses or voltage signals from the feedback device each of which corresponds to a predetermined unit change in angular or rotational position of the motor. As the axis includes a mechanism that translates the motor shaft rotation into linear or angular movement of the load, the current position of the load can be calculated based on the current angle of the feedback device and the total revolutions of the device tracked and recorded by the controller. It should be noted that a linear motor and a linear encoder or any combination of suitable motors and feedback devices can be used.

The controller 114, 214 may include a memory, a processor, and an input and output (I/O) device. The memory stores programs or algorithms including servo loop control algorithms and other programs for operation of various motion axes. Dimensional data of fixed structural features or hardstops in the radiation system may be provided to the controller and stored in the memory. For example, the value of distance between the hardstops for a linear axis, or the value of angle between hardstops for a rotational axis may be provided to and stored in the controller's memory. The processor executes the programs and generates commands for operation of the motion axes. The controller receives signals from the feedback devices and sensors and sends signals such as voltage and current output to command the motor via the input and output (I/O) device or system.

The controller 114, 214 may be programmed to execute a servo loop algorithm such as a torque control, velocity control or position control etc., and modify the current or voltage output to the motor based on the feedback from the feedback devices. For instance, based on the actual feedback position and the desired position of the motor or the load, the controller may produce a power output required to drive the motor or the load to a desired position. The controller may be programmed to monitor the magnitude change pattern of the motor's electrical parameters such as the motor current and back EMF etc. during the motion of the axis toward a hardstop, and compare the monitored value with a predetermined value stored in the controller. The controller may monitor current using electronic circuitry designed to allow direct reading of the current sent to the motor. The controller may also be programmed to monitor the motor feedback device or load feedback device during the motion of the axis toward a hardstop. The velocity of the motor or the load may be measured by monitoring back EMF or the feedback devices coupled to the motor or load and compared with a predetermined value stored in the controller. Various methods are known by which the controller can determine velocity from feedback devices. For example, when position-based feedback devices such as encoders, resolvers, a series of Hall sensors, or potentiometers are used, the controller may compute velocity from the position difference over a given time period. With velocity-based feedback devices such as a tachometer, the controller may compute velocity from the direct feedback value times a given proportionality constant. The controller can also determine velocity using the motor's electronic characteristic of back EMF. The controller may include electronic circuitry for determining both the voltage supplied to the motor and the return voltage. By comparing these voltages along with known motor constants, the controller can compute the motor velocity. In cases where the system includes limit switches which signal the controller that the axis is approaching its end of travel, the controller may also be programmed to reduce the axis speed and lower the peak torque capacity of the motor to avoid collision damage to the axis and improve the accuracy of measurement. The controller may be programmed to execute a homing routine to establish a home position for an axis and record the home position. The controller may capture signals from the feedback devices or sensors which are indicative of the current position of the motor or the load, and calculate the current position of the motor or the load with reference to the home position that has been established. The controller may be programmed to generate alert or warning messages if it determines that certain faults occur.

Figure 3:
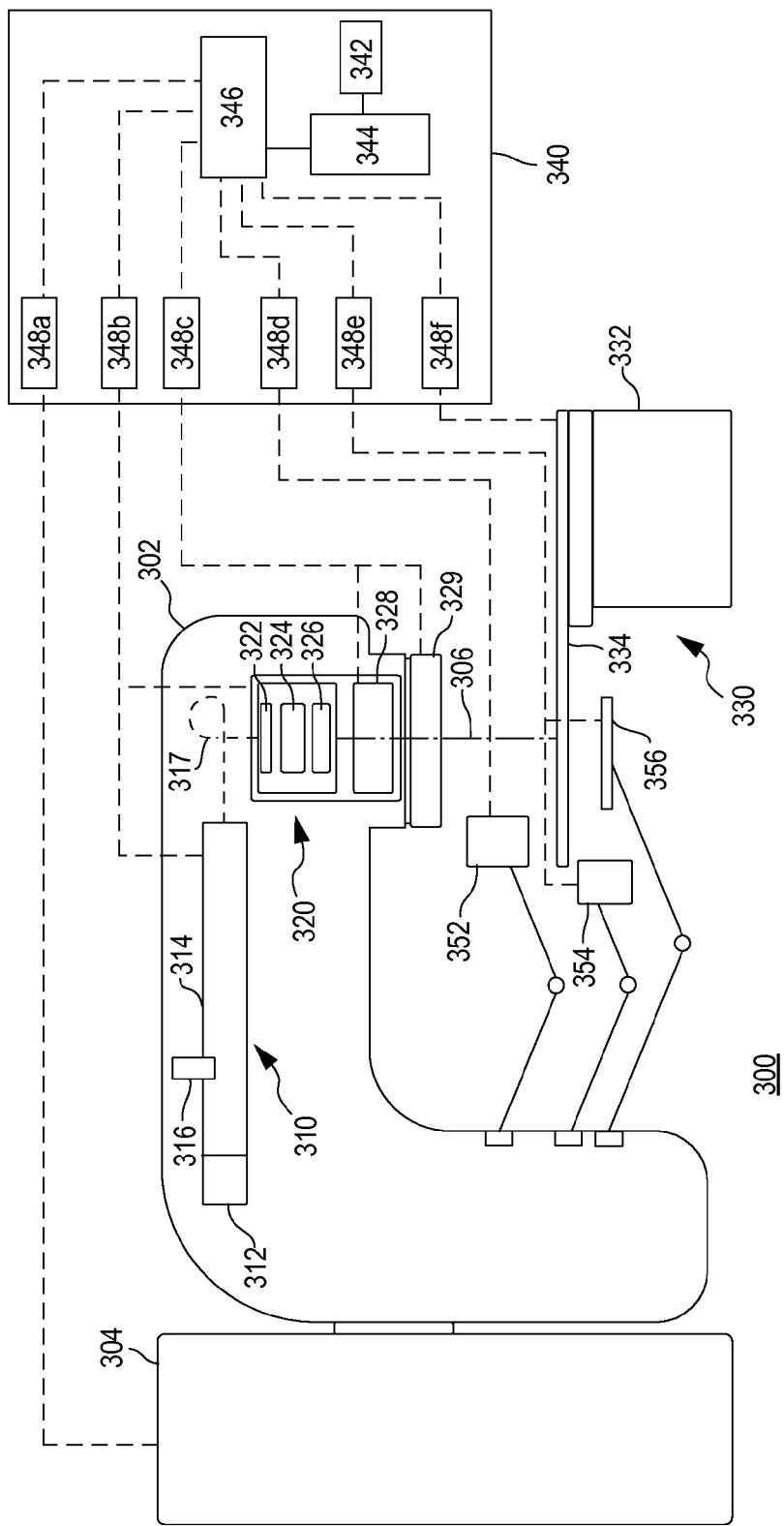
FIG. 3 is a schematic representation of a radiation system in accordance with some embodiments of the disclosure.

FIG. 3 is a schematic representation of an exemplary radiation system 300 that can embody the principle of the disclosure. In general, the radiation system 300 may include a linear accelerator system 310, a treatment head 320, a patient support system 330, and a control system 340. The linear accelerator system 310 and the treatment head 320 may be supported and enclosed in a gantry 302, which may be rotatably supported by a stand 304. The radiation system may optionally include various devices for image acquisition 352, 354, 356.

The linear accelerator system 310 may include an electron gun 312 configured to produce and inject electrons into an accelerator guide 314, which may have a plurality of accelerating cavities coupled with pulsed microwave energies. An energy switch assembly 316 may be mounted to the accelerator guide 314 operable to assist in modulating the energy levels of output electron beams 316. The output electron beam 317 may be directed to the treatment head 320 which may house various device assemblies configured to produce, shape, or monitor treatment beams. A target assembly 322 may include one or more targets configured to produce X-rays upon impingement by electrons. The target assembly 322 may be moved with a linear and/or a rotational axis to position a target relative to a beam line 306. In a photon or an SRS mode operation, a target may be positioned in the beam path for producing X-ray radiation. In an electron mode operation, the target may be moved out of the beam path to allow an electron beam to pass unimpeded. In alternative embodiments, the target assembly 322 may reside outside the treatment head 320.

A beam filter assembly 324 may support one or more collimators, and optionally one or more photon flattening filters and one or more electron scattering foils. The beam filter assembly 324 may also support other devices such as field light mirror etc., as will be described in greater detail below. The collimators supported by the beam filter assembly may have a conically or cylindrically shaped hole configured to define a treatment beam useful e.g. in radiosurgery, stereotactic radiosurgery, or any other forms of radiation therapy. The photon flattening filter may shape radiation to provide a uniform dose distribution across the radiation field. The electron scattering foil may scatter incident electrons to provide a broadened, uniform profile of a treatment beam.

The beam filter assembly 324 can be moved for positioning a collimator, a photon flattening filter, or an electron scattering foil relative to the beam path. The beam filter assembly can be moved by one or more and in some instances two or more motion axes. For example, the beam filter assembly may be moved by two linear axes in orthogonal directions (e.g. in X-Y). The beam filter assembly may also be moved by a combination of a linear axis and a rotational axis. By way of example, the beam filter assembly may be moved by a linear axis and a rotation axis, in which the rotational axis may be supported and further translated by the linear axis. Alternatively, the beam filter assembly may be moved by a linear axis and a rotational axis, in which the linear axis may be supported and further rotated by the rotational axis.

Ion chamber assembly 326 may include ion chambers configured to measure the parameters of a treatment beam such as beam energy, dose distribution, and dose rate etc. The ion chamber assembly 326 may be moved with a linear axis and/or a rotational axis relative to the beam path. In an SRS or a photon mode operation, the ion chambers 326 may be positioned under an SRS collimator or a photon flattening filter for measuring the parameters of a radiation beam. In an electron mode operation, the ion chambers may be positioned under an electron scattering foil in the beam centerline for detecting the parameters of an electron beam.

Collimation assembly 328 may include upper collimator jaws and lower collimator jaws each of which may be moved by a linear or rotational axis to provide secondary collimation. The linear or rotational axes for the lower or upper collimator jaws may be independently controlled. The upper and lower collimator jaws may be housed in an enclosure and rotated by a rotational axis.

Multileaf collimator (MLC) 329 may include a plurality of individual leaves each of which may be moved with a linear axis. By moving individual leaves to selected positions in a controlled manner, the size and shape of the treatment beam can be controlled.

Patient support system 330 may include a base 332 and a couch top 334. Linear axes may move the couch top 334 in the lateral (x-axis) and/or longitudinal (y-axis) directions. Linear axis may also move the base 332 vertically so that the couch top 334 may be moved in the vertical directions (z-axis). Rotational axes may rotate the couch 334 about an isocenter to provide a different couch angle relative to the radiation source, or rotate the couch top 334 to provide pitch, yaw, and/or roll rotation.

The radiation system 300 may optionally include devices for imaging such as imaging source 352, image acquisition devices 354 and 356 for use with keV or MV sources. Various linear and/or rotational axes may be used to move the sources and image acquisition devices in linear and/or angular directions.

Control system 340 controls the operation of the radiation system 300, preferably with a computer user interface 342. The control system 340 may include a processor 344 such as a digital signal processor, a field programmable gate array, a central processing unit, or a microprocessor. The processor 344 may execute programs and generate signals for operation of the motion axes and other devices or assemblies of the accelerator system. In some embodiments, the control system 340 may include a main control unit 346 which may supervise or regulate a plurality of controllers or nodes or sub-nodes 348a-348f. Each controller or node 348a-348f may be configured to control one or more motion axes for moving or positioning one or more devices. Responsive to the commands from a controller, one or more motion axes may move one or more devices or assemblies such as an energy switch, a target, an SRS collimator, a photon filter, an electron scattering foil, field light units, a treatment couch, imaging units etc. in a controlled and automatic manner based on a plan or routine, or based on the input from a user. The controller 348a-348f may receive signals from feedback devices, sensors, or from other devices such as the ion chambers, and generate commands for adjustment when necessary. For example, based on the beam parameter signals provided by the ion chamber 326, the control system 340 may recalculate and generate commands for adjustment to various motion axes. The motion axes may respond and adjust automatically the positions e.g. of the energy switch, target, SRS collimators, photon filters, or electron foils etc.

Figure 4:
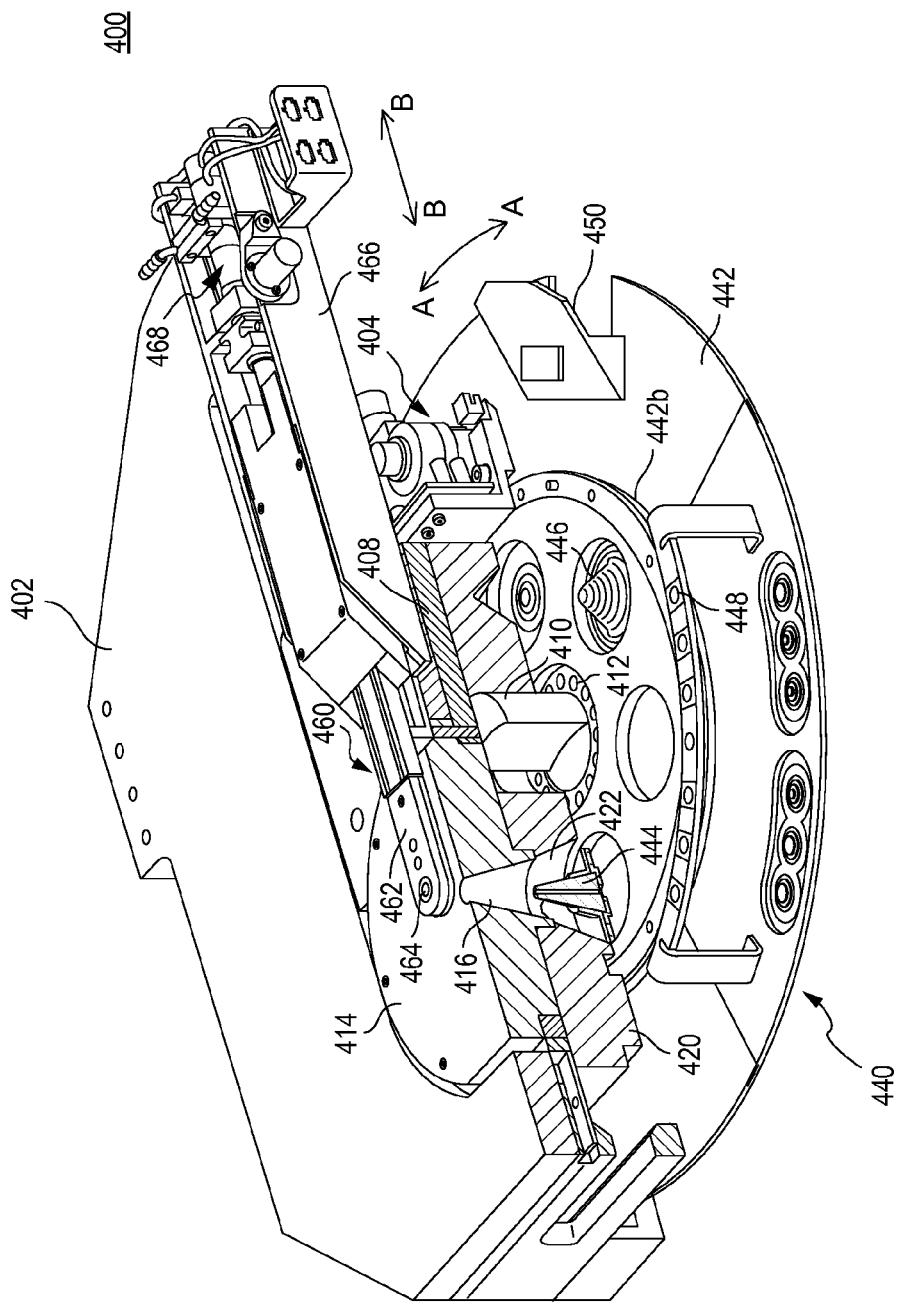
FIG. 4 illustrates an assembly in accordance with some embodiments of the disclosure with a cut-away view showing the construction of the assembly.
Figure 5:
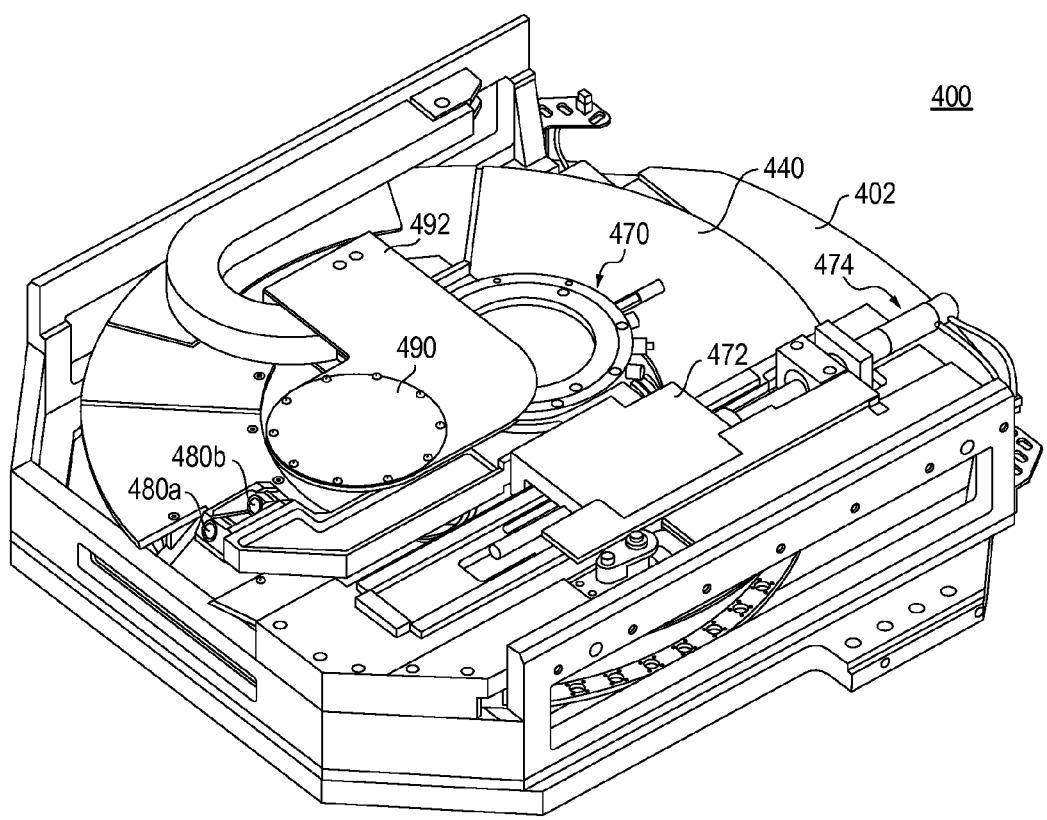
FIG. 5 is a bottom perspective view of an assembly in accordance with some embodiments of the disclosure.
Figure 6:
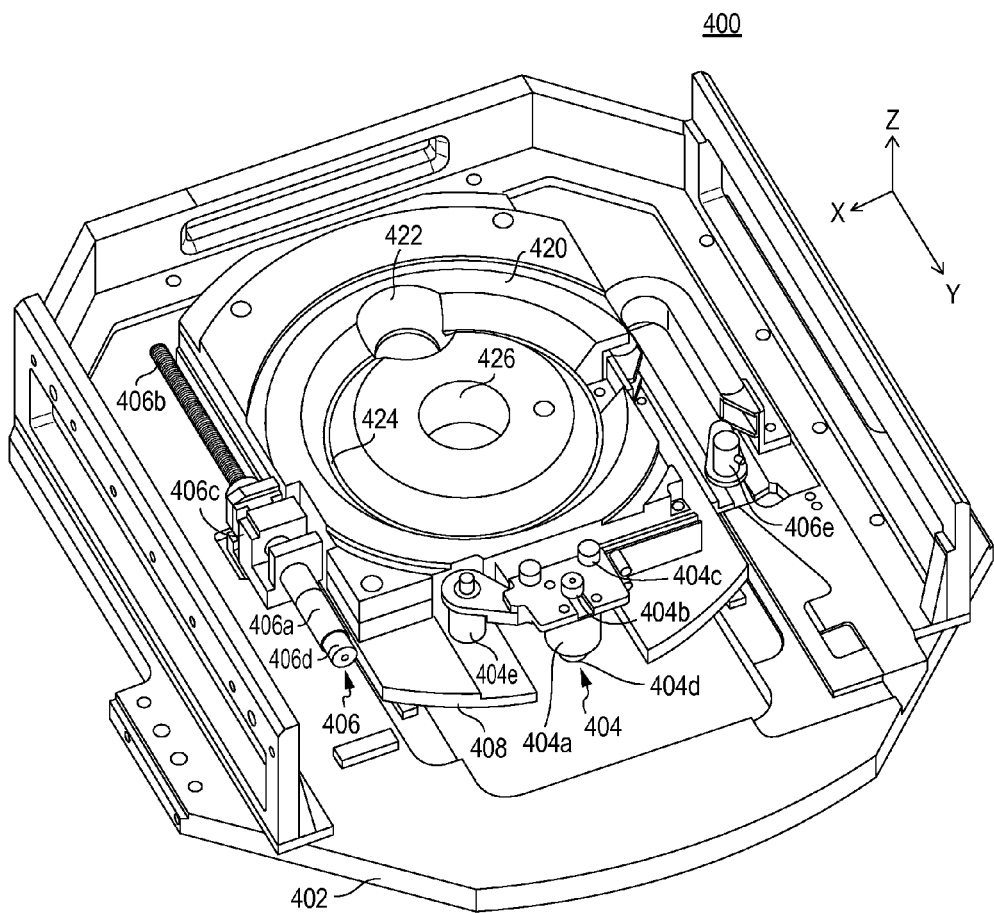
FIG. 6 is a bottom perspective view of an assembly in accordance with some embodiments of the disclosure; the ion chamber and beam filters are not installed in FIG. 6 for clarity of showing the embodiments.

FIGS. 4, 5, and 6 illustrate an assembly 400 of this disclosure. FIG. 4 is a cut-away view of the assembly 400 showing various components or devices. FIG. 5 is a bottom view of the assembly 400 showing additional components or devices. FIG. 6 is bottom view of the assembly 400, with some devices or components not shown for clarity of showing additional devices or components. In general, the assembly 400 includes a beam filter assembly 440 including a body member 442 supporting various components such as SRS collimators 444, photon flattening filters 446, electron scattering foils 448, and field light mirror 450, etc. The assembly 400 may also include a target assembly 460 including a substrate 462 supporting one or more targets 464. As shown in FIG. 5, the assembly 400 may further include an ion chamber assembly 470, a field light projector 480, and a backscatter filter 490. The assembly may be supported by a supporting structure 402 and mounted in a treatment head of a radiation system illustrated in FIG. 3.

The beam filter assembly 440 may be moved in an angular direction as indicated by arrow A-A. The beam filter assembly 440 may also be moved in a linear direction as indicated by arrow B-B. The angular movement of the beam filter assembly 440 can be accomplished by the rotational axis 404, which may be supported by a stage 408. The linear movement of the beam filter assembly 440 can be accomplished by a linear axis 406 (FIG. 6), which may be supported by the support body 402. In this embodiment, the rotational axis 404, which is supported by the stage 408, may be further moved by the linear axis 406. By moving the beam filter assembly 440 using a combination of the rotational axis 404 and the linear axis 406, a collimator 444, a photon flattening filter 446, an electron scattering foil 448 or a mirror 450 can be positioned relative to a beam centerline based on a selected mode operation. While a combination of a linear axis and a rotational axis is shown and described for illustration purpose, it should be noted that the beam filter assembly 440 can also be moved by a combination of two or more linear axes.

The beam filter assembly 440 may be secured to the stage 408 via a body member 410. The body member 410 may be fixedly attached to the stage 408 via any suitable means such as e.g. pins, screws etc. The rigid attachment to the stage 408 by the body member 410 allows the beam filter assembly 440 to move with the stage 408. The body member 410 can be further rotatably coupled to the beam filter assembly 440 via a bearing assembly 412. The bearing assembly 412 allows the beam filter assembly 440 to rotate in an angular direction.

FIG. 6 shows the exemplary stage 408 and linear axis 406 in greater detail. For clarity, the beam filter assembly 440, which is shown in FIG. 4, is not shown in FIG. 6. The linear axis 406, which may include a motor 406a and a ball screw 406b, can be secured to the supporting structure 402 via a mount 406c. The motor 406a operates to drive the ball screw 406b, which engages and thus moves the stage 408 and the beam filter assembly 440 attached to the stage in a linear direction. Guide rails and other mechanisms may be used to define the linear movement of the stage 408. A feedback device 406d may be coupled to the motor 406a to provide primary feedback on the position of the ball screw 406b. A separate feedback device 406e may be used to provide redundant or secondary feedback. The motor 406a can be a servo motor electrically connected to a controller which is operable with user interface software.

FIG. 6 also shows the rotational axis 404 in greater detail. The rotational axis 404, which may include a motor 404a, a pulley 404b, and roller guides 404c etc., may be supported by a support body, which may be secured to the stage 408 by any suitable means. A timing belt (not shown) may be wound around the pulley 440b and the beam filter assembly structure 442b. When actuated, the motor 404a drives the pulley 404b to turn, which transmits the rotation force to the timing belt. The timing belt engages beam filter assembly 442b and rotates it in an angular direction. The roller guides 404c can be adjusted to control the timing belt tension. A feedback device 404d coupled to the motor 404a may provide primary control feedback. A second housed resolver 404e may be used to provide redundant or secondary feedback. While a specific motor, roller guides, and feedbacks are described in detail for illustrative purposes, other types of drive mechanisms or feedback devices can also be used in the motion axes.

Returning to FIG. 4, the stage 408 may be configured to support a primary collimator 414. The stage 408 may have an opening for receiving the primary collimator 414, which may have a shape such as having a step at the bottom to fit in the opening and held in place. Suitable means such as pins, screws, etc. can be used to secure the primary collimator 414 to the stage 408. The primary collimator 414 can be made from tungsten or other suitable high density metals. Passageway 416 e.g. in a conical shape may be provided in the primary collimator 414 to generally define the field of radiation. The stage 408 may also support shielding 420. Shielding 420 may be located under the stage 408 and can be attached to the stage 408 by any suitable means such as pins, screws etc. Shielding 420 may be provided with a passageway 422 e.g. in a conical shape that may extend from and align with the passageway 416 in the primary collimator 414. Therefore, the primary collimator 414 and shielding 420 may be moved with the stage 408, for example, away from the beam centerline in electron mode or field light simulation operation.

Referring to FIG. 6, the shielding 420 may be provided with a channel 424 on the bottom side to provide a travel path or clearance for SRS collimators 444 and photon filters 446 while rotating in an angular direction. Opening 426 in the shielding 420 allows the body member 410 to pass through to secure the beam filter assembly 440 to the stage 408.

Figure 7:
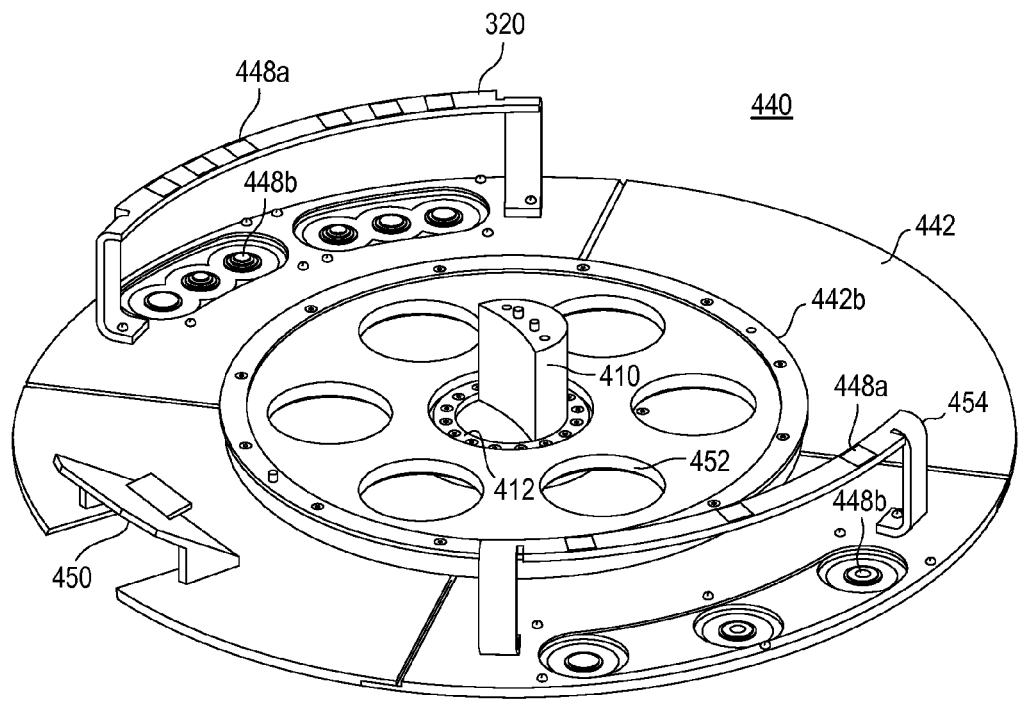
FIG. 7 is a perspective view of a beam filter device in accordance with some embodiments of the disclosure.

FIG. 7 shows a perspective view of a beam filter assembly 440 of this disclosure. For clarity, collimators and photon flattening filters are not shown in FIG. 7. The beam filter assembly 440 may have one or more ports or openings 452 configured to receive one or more SRS collimators 444 and/or one or more photon flattening filters 446. The beam filter assembly 440 may also support electron scattering foils 448. The SRS collimators 444, photon flattening filters 446 and electron scattering foils 448 can be arranged in any suitable configurations. In some preferred embodiments, the SRS collimators 444 and photon flattening filters 446 may be arranged in a circular or an arc configuration having a first radius. Six ports are shown in FIG. 7 for positioning the collimators 444 and/or photon flattening filters 446. It will be appreciated that a different number of ports can be provided. The scattering foils 448 may be arranged in a circular or an arc configuration having a second radius. The second radius is preferably different from the first radius. For example, the electron scattering foils 448 may be arranged outer of the SRS collimators 444 and photon flattening filters 446. Alternatively, the SRS collimators 444 and photon flattening filters 446 may be arranged outer of the electron scattering foils 448.

The photon flattening filters 446 can be in various forms including e.g. conical form. The conical photon filters can be held in the ports 452 by any suitable means such as pins, screws etc. The conical filters 446 may point upwards towards the radiation source or downwards. The materials, forms and/or configuration of the photon flattening filters 446 can be chosen to match the energy of the X-rays produced based on specific applications.

The electron scattering foils 448 may include primary scattering foils 448a and secondary scattering foils 448b. The combination of primary and secondary scattering foil pairs 448a, 448b may provide a broadened, uniform profile of a treatment beam. Nine pairs of electron scattering foils are shown in FIG. 7, six grouped together on one side and three grouped together on the opposite side. It will be appreciated that a different number of electron scattering foils can be provided. The primary foils 448a and secondary foils 448b may be arranged at different elevations by a structure 454 mounted to the body member 442. The structure 454 may raise the primary foils 448a above the secondary foils 448b and vertically aligns a primary foil 448a with a secondary foil 448b. The increased distance between the primary and secondary scattering foils allows the primary scattering foils to be higher in the treatment head and closer to the same elevation or location where the photon source (the target) is located. Having the source of electrons and the source of photons at an about same location is desirable since treatment planning and other design aspects of the treatment head are generally optimized around the location of the photon source. The increased separation between the primary and secondary electron foils also makes electron beam performance less sensitive to small machining variations in the thickness of the secondary foils and in the separation distance. An electron foil assembly with small separation between the upper and lower foils requires tighter tolerances on spacing and thickness of the lower foils to achieve uniform electron beam performance.

Figure 8:
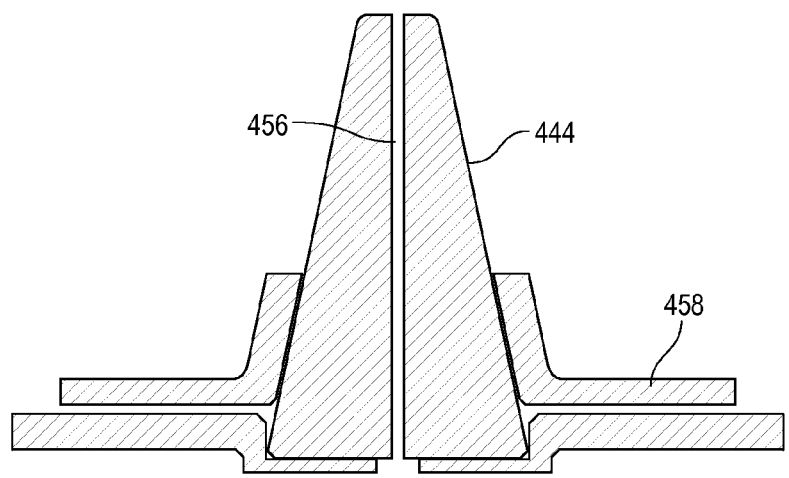
FIG. 8 is a cross-sectional view of an SRS collimators in accordance with some embodiments of the disclosure.

FIG. 8 is a cross-sectional view of a SRS collimator 444 that can be supported or carried by the beam filter assembly 440 of this disclosure. The SRS collimator 444 can be made from tungsten or any other suitable high density materials. The SRS collimator 444 can be provided with a passageway 456 for shaping the radiation passing there through. In general, the collimator passageway 456 can be in any configurations for providing any desired shape of treatment beams. By way of example, the SRS collimator 444 may have a conically-, cylindrically-, or trapezoidally-shaped hole. In some embodiments, the size of the collimator passageway can be machined such that the provided treatment beams are suitable for radiosurgery such as stereotactic radiosurgery. Precision electrical discharge machining (EDM) or other suitable techniques known in the art can be used in manufacturing the collimators. By way of example, collimators may have a passageway 456 sized to provide a treatment beam with a projected opening with a largest dimension of 1, 2, 3, 4, 5, 6, 8, 10, 12, 15, or 20, 25, or 30 mm.

The outer dimension of the SRS collimators 444 can be in any shape such as conical, hemi-spherical, cylindrical, trapezoidal, or rectangular etc. Preferably the collimator 444 may have an outer shape and dimension that help provide shielding coverage. Separate members 458 may be used to provide additional shielding and secure the collimator in the ports on the beam filter assembly.

A combination of the linear axis and rotational axis or other combination of motion axes allow for automated adjustments of the position of SRS collimators, photon flattening filters, and electron scattering foils. Motorized axes may be controlled by a computer and adjustments can be made using a software interface rather than manual adjustment as in the prior art. With a suitable 2D radiation sensor (such as a grid ion chamber array) and an automated tuning software application, these adjustments can be made without human intervention. This eliminates the need for medical physicists or radiation therapist to manually load or unload SRS cones or cone mount, which in turn minimize the amount of manual quality assurance (QA). Furthermore, since the SRS collimators can be placed within a beam filter assembly mounted in the treatment head, a potential source of collision is removed. In conventional radiation machines, SRS cones are externally mounted, which may present a potential hazard of collision with the treatment couch or the patient. It will be appreciated by one of ordinary skill in the art that the SRS collimators described herein can be moved and positioned by any number of mechanisms. The specific devices and mechanisms described above are provided for illustration purpose and therefore the present claims are not so limited.

The use of two or more motion axes such as a rotational axis and a linear axis to adjust the position of SRS collimators 444, photon flattening filters 446, and electron scattering foils 448 makes it practical to place the collimators, photon filters, and electron scattering foils at a different radius of a beam filter assembly 440. To position the SRS collimators, photon filters and electron scattering foils at two or more different radii allows for a greater number of collimators, filters or foils available at two or more radii, as compared to confining the collimators, filters and foils at a same radius. A greater selection of collimators, filters, and foils may allow for a greater selection of X-ray and electron energies and radiotherapy applications.

The two-radius design also allows for a smaller inner radius for the SRS collimators 444 and photon flattening filters 446. A smaller inner radius of a travel path would introduce a greater curvature in the shielding gaps, hence substantially reducing the direct radiation leakage paths which would otherwise require heavy and expensive shielding plugs.

The use of a separate inner radius for SRS collimators and photon filters allows for a large, simple and effective primary collimator 414. Prior art designs have significant compromises to the primary collimator below the target. In most prior designs, the primary collimator is fixed and chopped up in complex and inefficient ways to allow motorized filters and foils to penetrate it. Earlier designs place primary collimator shielding further from the radiation target requiring significantly greater mass, complexity and cost of shielding components.

Returning to FIG. 4, the assembly 400 may further include a target assembly 460. The target assembly 460 positions a target in the beam path for generation of X-rays in an SRS mode or a photon mode, or moves a target out of the beam path in an electron mode. The target assembly 460 includes a substrate 462 and one or more target buttons 464 supported by the substrate. The target assembly 460 can be fixedly attached to the base plate 402 via a mount 466. The target assembly 460 can be driven by a linear axis 468. Alternatively, the target assembly may be driven by a rotational axis. The linear axis 468 may be similar to the linear axis 406 described above in connection with the stage 408, and thus detail description of its construction and operation is omitted. The target assembly 460 may include one or more targets each being optimized for the energy of an incident electron beam. For example, the target assembly 460 may include a first target adapted for an SRS mode, a second target for a photon mode, a third target for a second SRS or second photon mode, etc. The material of a target can be chosen and/or the thickness of a target be optimized for an incident electron beam with a particular energy level. In operation, the linear axis 468 moves or positions one of the targets in the beam path for an SRS mode or a photon mode operation. In an electron mode, the linear axis 468 removes the targets 464 out of the beam path to allow an electron beam passes unimpeded.

Figure 9:
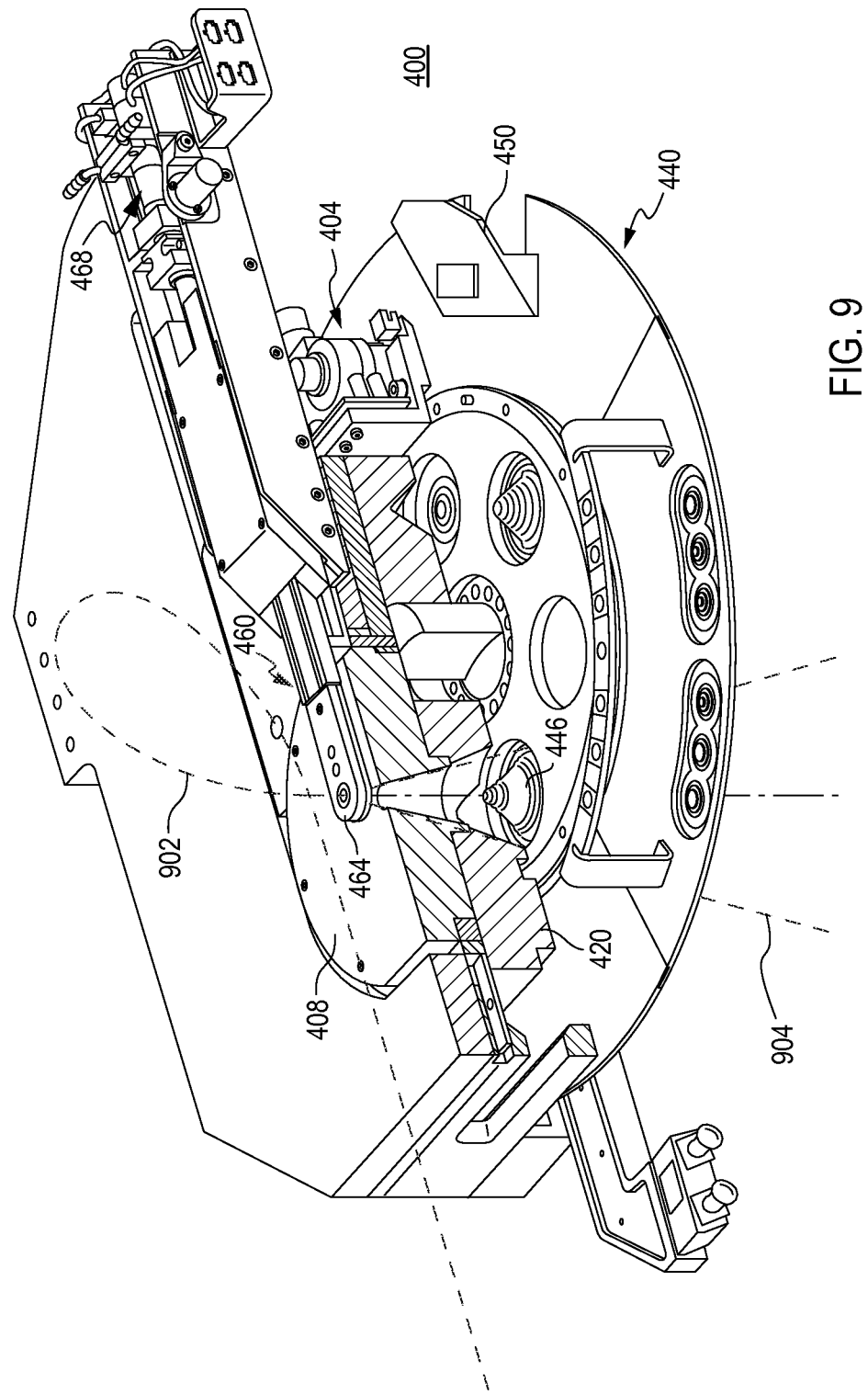
FIG. 9 illustrates an exemplary assembly in a photon mode in accordance with some embodiments of the disclosure.

FIG. 9 illustrates an exemplary assembly 400 in a photon mode operation in accordance with some embodiments of the disclosure. The primary collimator 408, shielding 420, ion chamber 470, and backscatter filter 490 have been positioned in the beam centerline using linear axis 406 and 474 respectively. Rotational axis 404 is actuated to move the filter-foil assembly 440 in an angular direction to align one of the photon flattening filters 446 in the beam centerline. Sequentially or simultaneously, the linear axis 468 is actuated to position a target button 464 in the beam centerline. An electron beam 902 impinges the target button 464 and X-rays 904 are produced. The field of X-rays 904 is shaped as the X-rays pass through the passageways in the primary collimator 408 and shielding 420. A radiation beam with a uniform dose distribution is obtained as the X-rays pass through a photon flattening filter 446. The parameters of the treatment beam are detected as the beam passes through the ion chamber 470. Backscatter filter 490 located under the ion chamber 470 blocks backscatter radiation from entering the ion chamber 470 to ensure accurate measurement of the radiation beam parameters. Because the mirror 450 is installed on the filter-foil assembly 440 and is off the beam centerline in the photon mode, the treatment beam generated pass downstream unimpeded by the mirror. Depending on the energy of an incident electron beam 902 for a particular application, the linear axis 468 may move the target assembly 460 to position a target button 464 that is optimized for such beam energy in the beam path for optimized performance of the target. Similarly, depending on the energy of an incident electron beam, the rotation axis 404 may rotate to position a flattening filter 446 that is optimized for such beam energy in the beam centerline for optimized performance of the filter.

Figure 10:
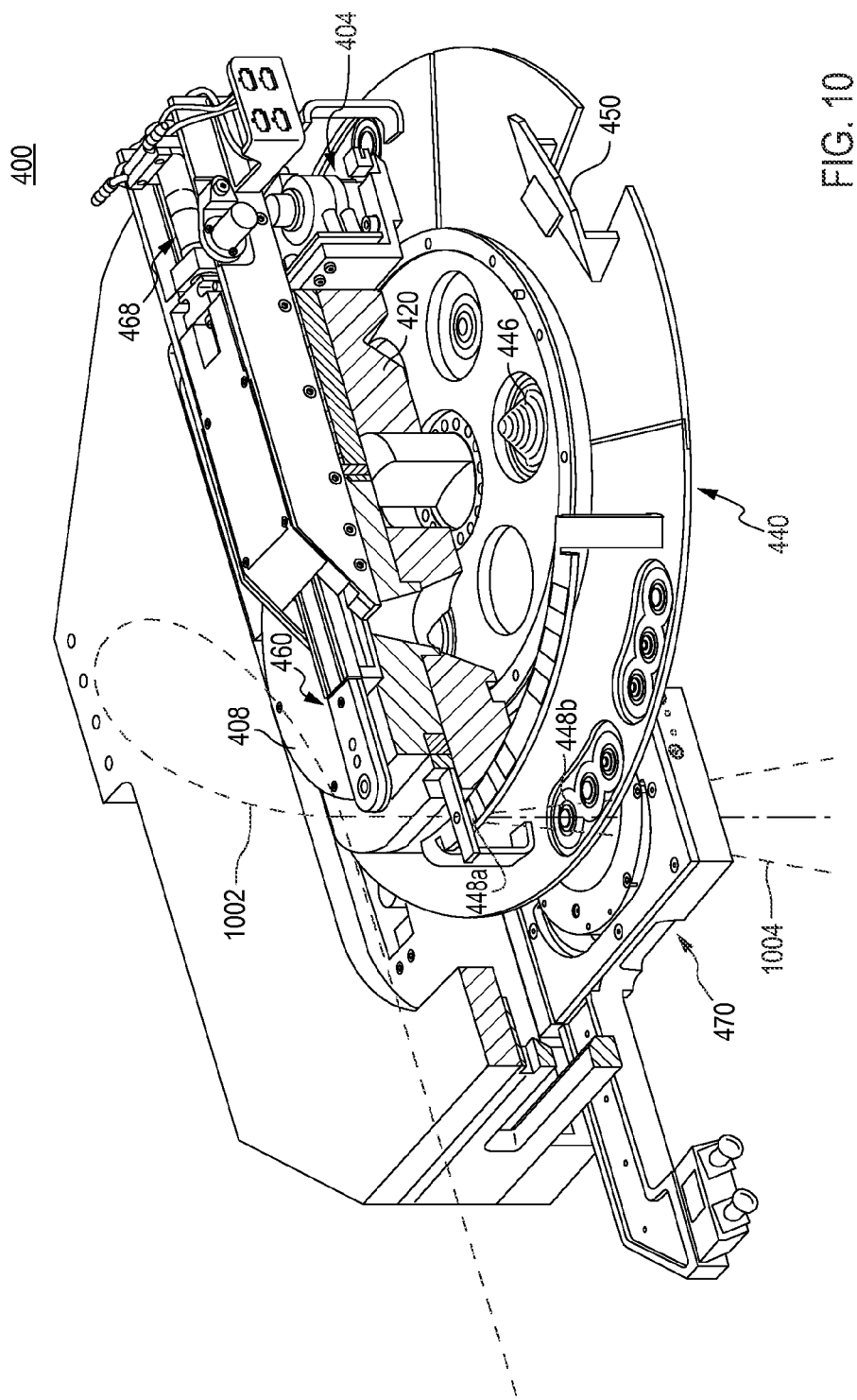
FIG. 10 illustrates an exemplary assembly in an electron mode in accordance with some embodiments of the disclosure.

FIG. 10 illustrates an exemplary assembly 400 in an electron mode in accordance with some embodiments of the disclosure. In an electron mode, linear axis 468 moves the target assembly 460 to retrieve the target from the beam centerline. Linear axis 406 drives the stage 408 to move the primary collimator 408, shielding 420, and backscatter filter 490 away from the beam centerline. Because the electron scattering foils 408 have a different or greater radius than the photon flattening filters 446 on the filter-foil assembly 440, driving the filter-foil assembly 440 to move the flattening filters 446 away from the beam centerline would bring the scattering foils 448 to the beam centerline. Rotational axis 404 moves the filter-foil assembly 440 in an angular direction to align one of the electron scattering foils 448 with the beam centerline. The primary and secondary scattering foils 448 scatter the electron beam to produce a broadened, uniform profile of a treatment beam 1004. Depending on the energy of an incident electron beam for a particular application, the rotational axis 404 may rotate the filter-foil assembly 440 to align a scattering foil that is optimized for such beam energy in the beam path for optimized performance of the foil. The parameters of the treatment beam are detected as the beam passes through the ion chamber 470.

Figure 11:
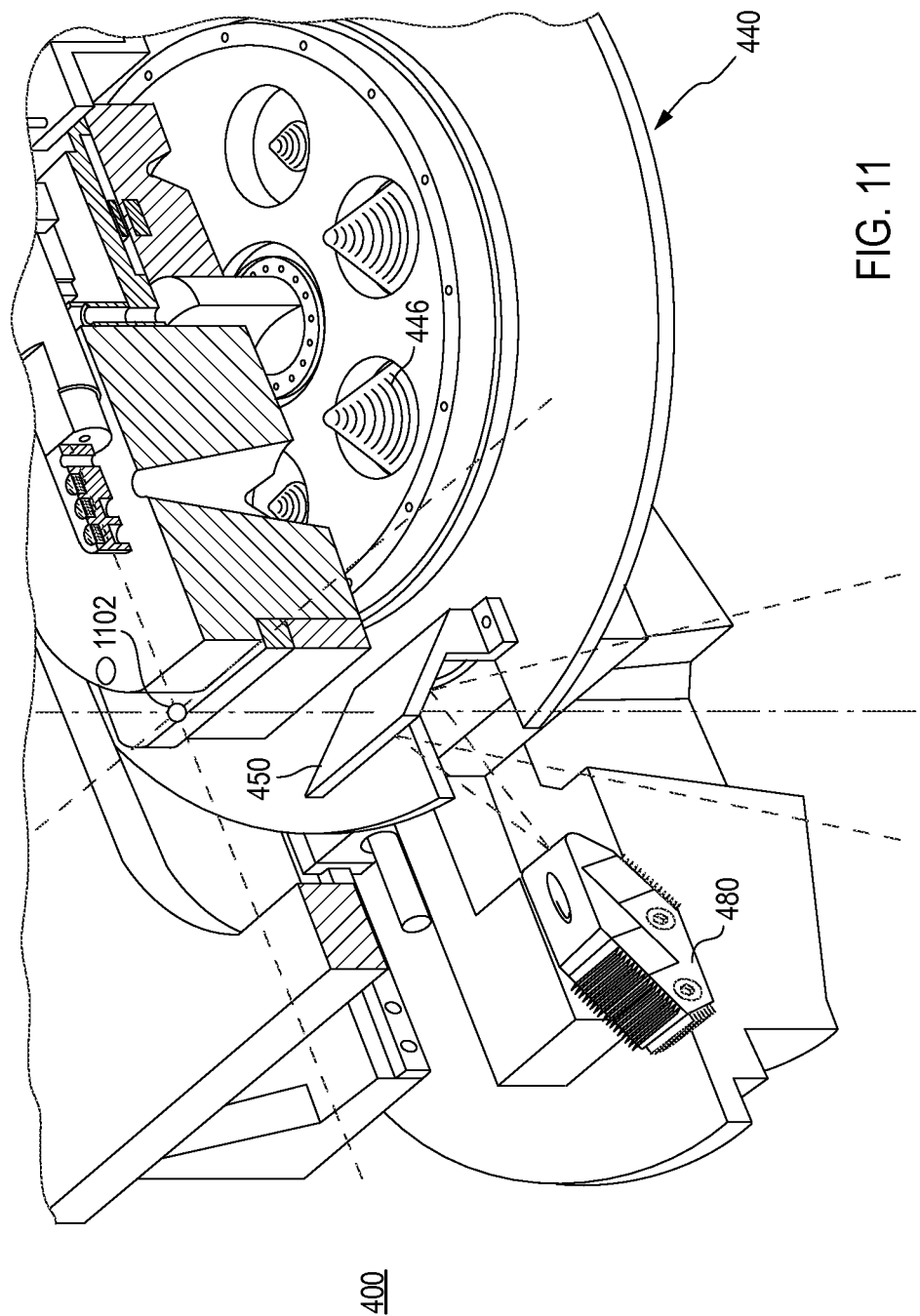
FIG. 11 illustrates an exemplary assembly in a field light simulation mode in accordance with some embodiments of the disclosure.

FIG. 11 illustrates an exemplary assembly 400 in a field light simulation mode in accordance with some embodiments of the disclosure. Linear axis 474 drives the ion chamber assembly 470 to move the ion chamber away from the beam centerline. Linear axis 406 drives the stage 408 to move the primary collimator, shielding, and backscatter filter away from the beam centerline. Because the mirror member 450 has a greater radius than the photon flattening filters 446 on the beam filter assembly 440, driving the beam filter assembly 440 to move the flattening filters 446 away from the beam centerline would bring the mirror member 450 to the beam centerline. Rotational axis 404 moves the beam filter assembly 440 in an angular direction to position the mirror 450 in the beam centerline. The ion chamber axis 474 moves and adjusts the position of a light source 480 to project the source to a virtual radiation source position 1102. Mirror 450 reflects light projected from the light source 480 to illuminate an area e.g. on the surface of a patient's skin for simulation.

Figure 12:
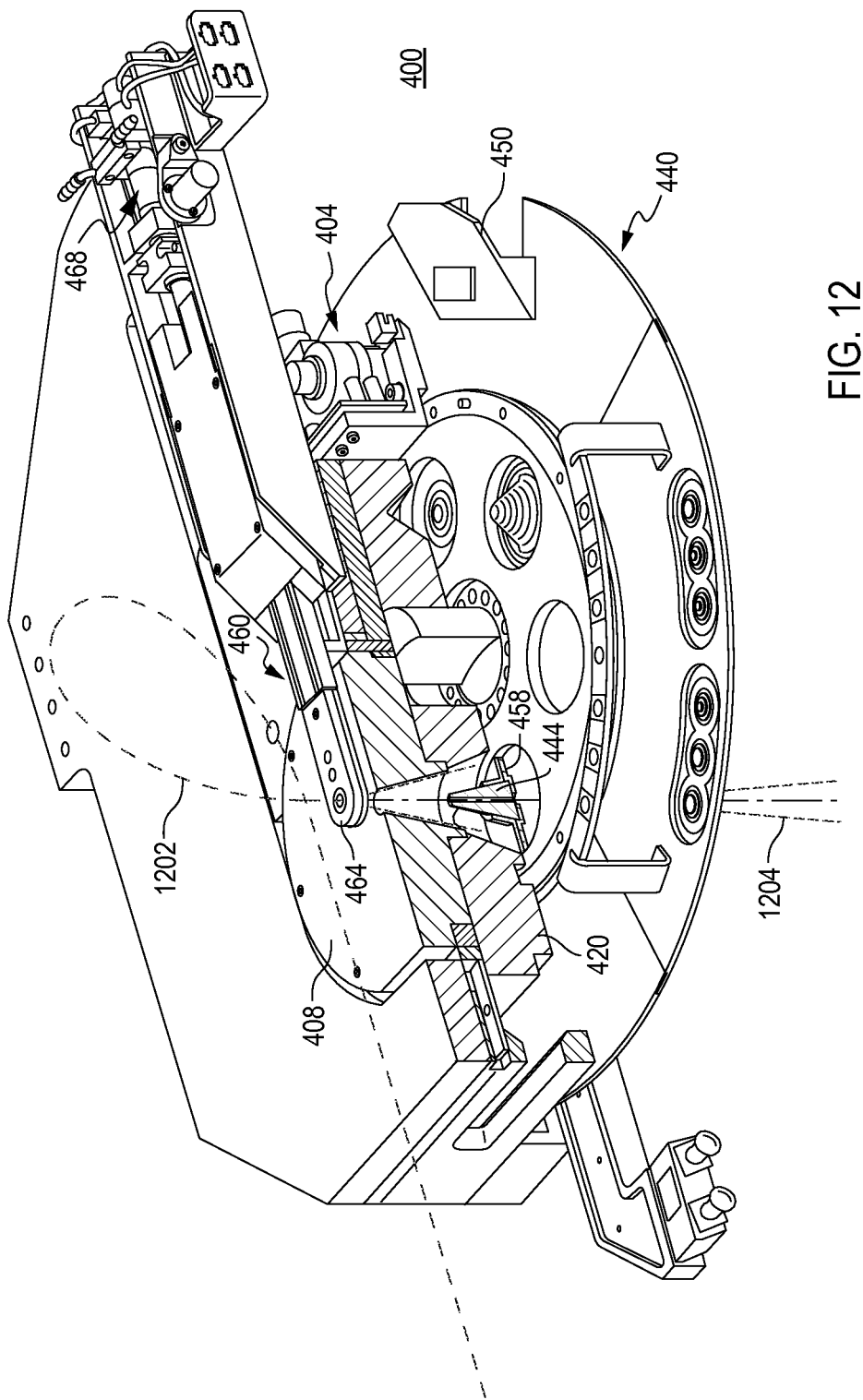
FIG. 12 illustrates an exemplary assembly in an SRS mode in accordance with some embodiments of the disclosure.
Figure 13A:
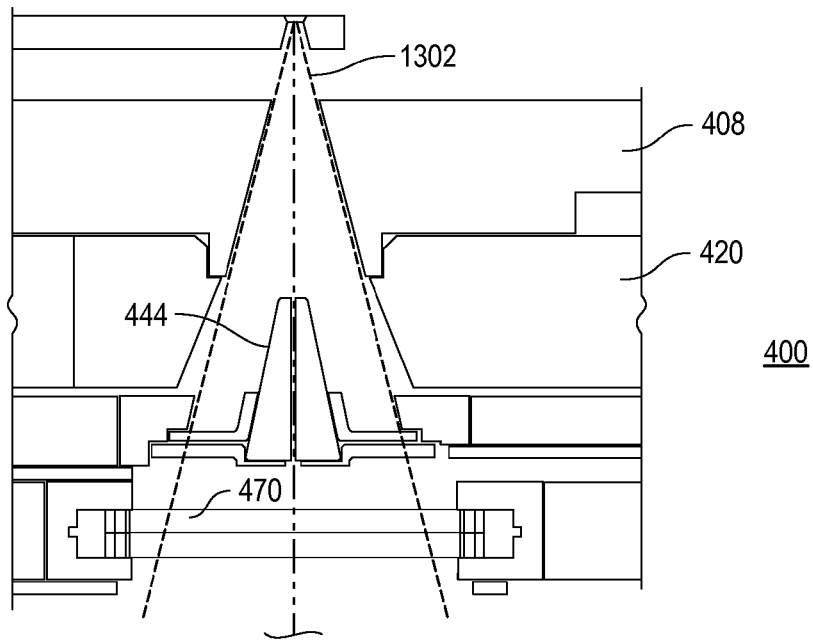
FIGS. 13A-13B illustrate beam collimation by an exemplary assembly and beam projection at the isocenter in accordance with some embodiments.
Figure 13B:
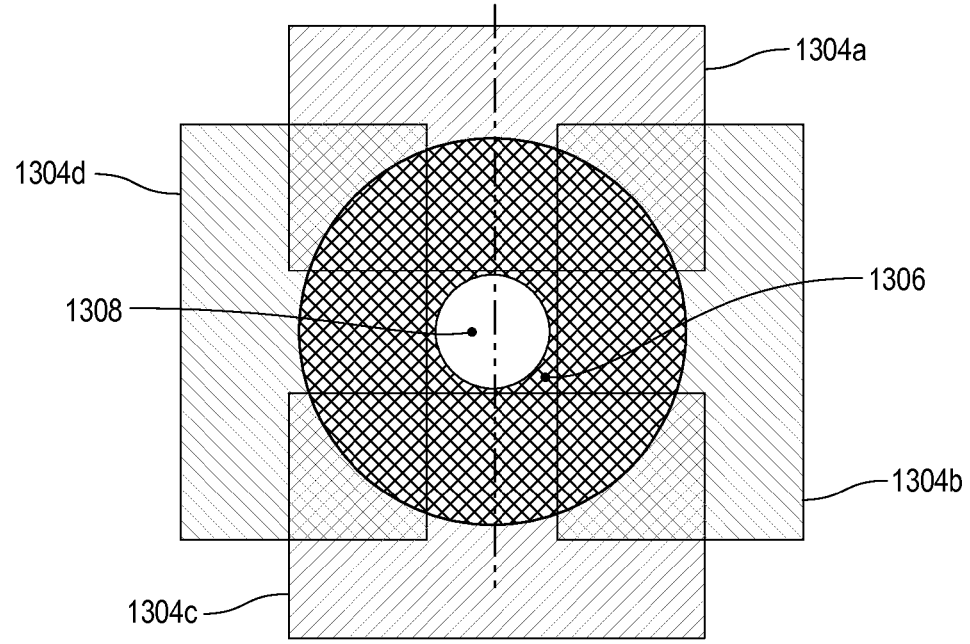

FIG. 12 illustrates an exemplary assembly 400 in an SRS mode operation in accordance with some embodiments of this disclosure. The primary collimator 408 and shielding 420 are positioned and aligned in the beam centerline. The ion chamber 470 and the backscatter filter 490 are also positioned in the beam centerline. Rotational axis 404 moves the beam filter assembly 440 in an angular direction to align an SRS collimator 444 in the beam centerline. Sequentially or simultaneously, the linear axis 468 is actuated to position a target button 464 in the beam centerline. An electron beam 1202 impinges the target button 464 and X-rays are produced. The field of X-rays is generally shaped as the X-rays pass through the primary collimator 408 and shielding 420. The field of radiation is further defined by the SRS collimator 444 to provide a focused treatment beam 1204, with a projected size that is suitable for radiosurgery or stereotactic radiosurgery. Additional collimation devices such as collimator jaws or MLC leaves may offer additional collimation of the treatment beam outside of the area shielded by the SRS collimator 444. FIG. 13A is a partial, cross-sectional view of the assembly 400 showing the collimation of the beam 1302 by the primary collimator 408, shielding 420, and SRS collimator 444. Additional collimator jaws (not shown in FIG. 13A) may offer additional collimation, providing a projected beam at the isocenter shown in FIG. 13B. In FIG. 13B, the four rectangular regions 1304a, 1304b, 1304c, and 1304d represent shielding provided by the collimator jaws. The annular region 1306 represents the shielding provided by the SRS collimator 444. The central circular region 1308 represents the focused treatment beam passing through the hole in the SRS collimator 444 and unimpeded by the collimator jaws.

Figures 14A, 14B:
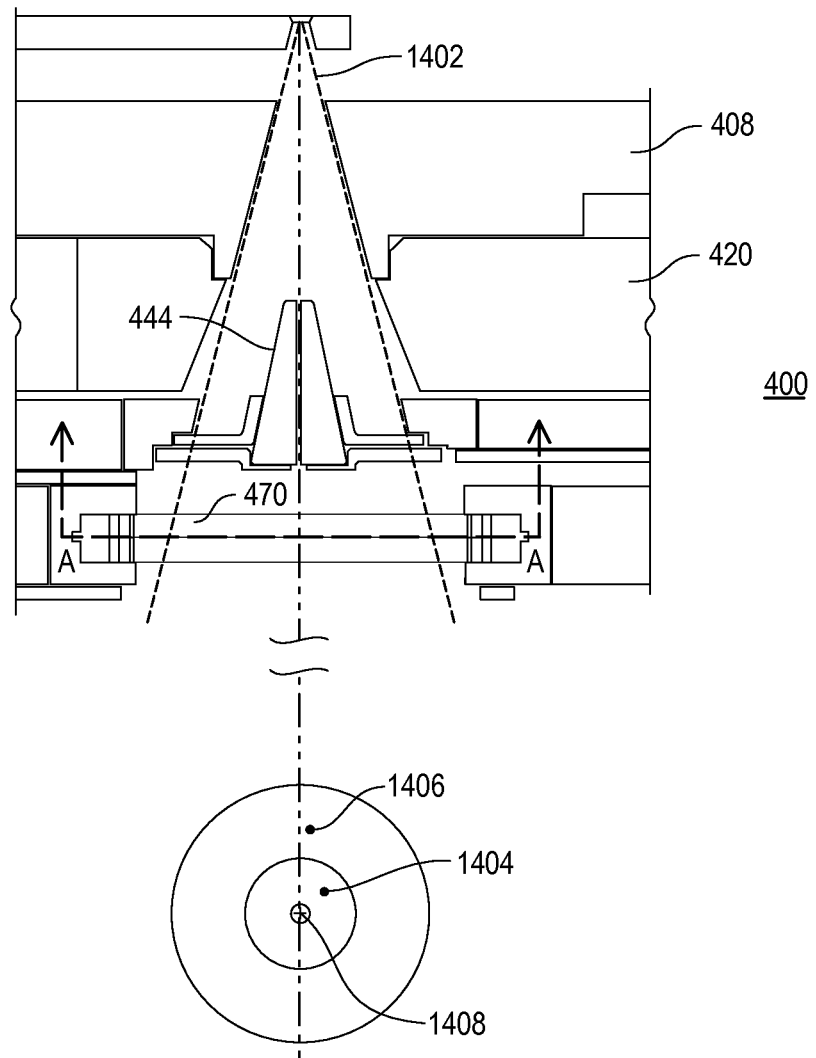
FIGS. 14A-14B illustrate beam collimation by an exemplary assembly and beam projection at an ion chamber in accordance with some embodiments.

The parameters of the treatment beam are detected as the beam passes through the ion chamber 470. FIG. 14A shows that the SRS collimator 444 can be shaped, mounted and/or supported in a way that allows projection of the treatment beam 1402 onto the ion chamber 470, allowing the ion chamber to be effectively used as a feedback and safety device. FIG. 14B illustrates the beam projection at the center of the ion chamber 470 at a cross-section taken along line A-A in FIG. 14A. The inner annular region 1404 represents beam attenuation by the SRS collimator 444 (e.g. 95% attenuation). The outer annular region 1406 represents the beam attenuation outside the area of the SRS collimator 444 (e.g. 0% attenuation). The central circular region 1408 represents the beam attenuation along the path of the hole in the SRS collimator 444 (e.g. 0% attenuation). The beam passing through the hole in the SRS collimator (1408) and outside the area of the SRS collimator (1406) is projected onto the ion chamber 470, providing sufficient beam for detection by the ion chamber 470. Backscatter filter 490 located under the ion chamber blocks backscatter radiation from entering the ion chamber to ensure accurate measurement of the radiation beam parameters.

One of the advantages of the assembly of the disclosure is that it can be configured to automatically adjust the position of collimators, beam filters, field light assembly, or other device components. The automatic adjustment can be accomplished by a control system operable by a computer software interface such as a Graphical User Interface (GUI). The control system may include a processor such as for example, a digital signal processor (DSL), a central processing unit (CPU), or a microprocessor (μP), and a memory coupled to the processor. The memory serves to store programs for the operation of the beam filter positioning device and other programs. The processor executes the program and generates signals for operation of the motion axes or other components of the assembly. Responsive to the signals from the control system, the assembly operates in which one or more motion axes move the collimators, beam filters, field light source, mirror, or other device components in a controlled and automatic manner based on a plan or routine, or based on a demand input from a user. The control system also receives feedback signals from sensors or resolvers in the motion axes, or from other device components such as the ion chamber, and generates signals for adjustment when necessary.

Exemplary embodiments of beam filter assemblies, radiation apparatuses, and radiation systems have been described. Those skilled in the art will appreciate that various modifications may be made within the spirit and scope of the invention. All these or other variations and modifications are contemplated by the inventors and within the scope of the invention.

What is claimed is:

1. An assembly comprising:
   a body,
   one or more collimators supported by the body, each of the one or more collimators having a through hole configured to define a shape or size of a treatment beam having a beam centerline, one or more photon flattening filters supported by the body, and one or more electron scattering foils supported by the body, wherein said one or more collimators and said one or more photon flattening filters are positioned in a circular or arc configuration having a first radius, and said one or more electron scattering foils are positioned in a circular or arc configuration having a second radius different from the first radius; and
   a first axis operable to move the body, and a second axis operable to move the body, wherein said first axis is a linear axis operable to translate the body and said second axis is a rotational axis operable to rotate the body about a line parallel to the beam centerline, wherein the first and second axes are operable to align one of the one or more collimators, photon flattening filters, or electron scattering foils with the treatment beam.

2. The assembly of claim 1, wherein said first axis is operable to translate the second axis.

3. The assembly of claim 1 wherein said second axis is operable to rotate the first axis.

4. The assembly of claim 1 further comprising a second axis operable to move the body, wherein said first and second axes are linear axes.

5. The assembly of claim 1 wherein said first axis is a linear axis operable to translate the body and said second axis is a rotational axis operable to rotate the body, and said first axis is further operable to translate the second axis.

6. The assembly of claim 1 further comprising a field light assembly comprising a mirror member and one or more light sources, said mirror member being supported by the body.

7. The assembly of claim 1 further comprising a target assembly comprising one or more targets configured to produce radiation upon impingement by electrons and a third axis operable to move the target assembly.

8. The assembly of claim 7 further comprising an ion chamber assembly and a fourth axis operable to move the ion chamber assembly, wherein each of the one or more collimators is configured to allow a portion of the treatment beam to pass through an outside area of the collimator to be projected onto and detected by the ion chamber.

9. The assembly of claim 1 wherein the first axis comprises a servo motor and one or more feedback devices.

10. The assembly of claim 1 wherein each of the one or more collimators has a conically-, cylindrically-, or trapezoidally-shaped hole configured to define a treatment beam for radiosurgery.

11. A radiation apparatus comprising a linear accelerator, a treatment head, and a gantry enclosing the linear accelerator and the treatment head, the radiation apparatus comprising:
   a radiation source configured to produce a treatment beam;
   a primary collimator configured to generally define a field of the treatment beam;
   one or more stereotactic radiosurgery (SRS) collimators supported by a body movable relative to the radiation source to align one of the one or more SRS Collimators with the treatment beam, each of the one or more SRS collimators having a through hole configured to further collimate the treatment beam to provide a beam suitable for radiosurgery, and each of the one or more SRS collimators having a size to allow a portion of the treatment beam to pass around an outside area of the each of the one or more SRS collimators to be projected onto an ion chamber;

the ion chamber configured to detect the portion of the treatment beam passing around the outside area of the each of the one or more SRS collimators; and one or more collimation jaws configured to block at least a portion of the treatment beam passing around the outside area of the each of the one or more SRS collimators and through the ion chambers.

12. The radiation apparatus of claim 11 wherein each of the one or more SRS collimators has a conically-, cylindrically-, or trapezoidally-shaped through hole to define the treatment beam.

13. The radiation apparatus of claim 11 wherein the radiation source comprises a target configured to produce radiation upon impingement by electrons, and said target resides in the treatment head.

14. The radiation apparatus of claim 11 wherein said one or more SRS collimators are movable relative to the radiation source.

15. The radiation apparatus of claim 11 further comprising one or more photon flattening filters and/or one or more electron scattering foils supported by the body; and
a first and a second axes operable to move the body.

16. The radiation apparatus of claim 15 wherein said one or more collimators and said one or more photon flattening filters are arranged in a circular or arc configuration having a first radius, said one or more electron scattering foils are arranged in a circular or arc configuration having a second radius different from the first radius.

17. The radiation apparatus of claim 16 wherein said first axis is a linear axis operable to translate the body and said second axis is a rotational axis operable to rotate the body.

18. The radiation apparatus of claim 17, wherein said first axis is operable to translate the second axis.

19. The radiation apparatus of claim 17 wherein said second axis is operable to rotate the first axis.

20. The radiation apparatus of claim 15 wherein the first and second axes are linear axes.

21. A radiation system comprising:
a radiation source operable to generate a radiation beam having a beam centerline;
an assembly comprising a body, one or more collimators supported by the body each having a through hole configured to define a shape or size of a treatment beam, one or more photon flattening filters supported by the body, and one or more electron scattering foils supported by the body, wherein said one or more collimators and said one or more photon flattening filters are positioned in a circular or arc configuration having a first radius, and said one or more electron scattering foils are positioned in a circular or arc configuration having a second radius different from the first radius, and a first and a second axes operable to move the body relative to the radiation source, each of the first and second axes comprising a servo motor, wherein said first axis is a linear axis operable to translate the body and said second axis is a rotational axis operable to rotate the body about a line parallel to the beam centerline, and the first and second axes are operable to align one of the one or more collimators, photon flattening filters, or electron scattering foils with the treatment beam; and
a controller programmed to control the servo motor of the first and second axes in moving the body to a desired position.

22. The radiation system of claim 21 wherein each of the first and a second axes further comprises one or more feedback devices, and the controller is further programmed to control the servo motor of the first and second axes based on at least signals from the one or more feedback devices.

23. The radiation system of claim 21, wherein said first axis is operable to translate the second axis.

24. The radiation system of claim 21 wherein said second axis is operable to rotate the first axis.

25. The radiation system of claim 21 wherein said one or more collimators have a conically-, cylindrically-, or trapezoidally-shaped hole configured to define a treatment beam suitable for radiosurgery.

26. The radiation system of claim 21 further comprising an ion chamber and a third axis operable to move the ion chamber, wherein said third axis comprises a servo motor and said controller is further programmed to control the servo motor of the third axis in driving the ion chamber, wherein each of the one or more collimators is configured to allow a portion of the treatment beam to pass through an outside area of the collimator to be projected onto and detected by the ion chamber.

27. The radiation system of claim 26 further comprising a field light simulation system comprising a light source and a mirror member, said mirror member being supported by the body and movable by the first and second axes, and said light source being movable by the third axis.

28. The radiation system of claim 27 wherein the radiation source comprises a target assembly comprising one or more targets each being configured to produce radiation upon impingement by electrons, and a fourth axis operable to move the target assembly for positioning the one or more targets, wherein said fourth axis comprises a servo motor and the controller is further programmed to control the servo motor of the fourth axis in driving the target assembly to a desired position.

* * * * *